United States Patent [19]
Trifiró et al.

[11] 3,983,073
[45] Sept. 28, 1976

[54] PROCESS FOR PREPARING A CATALYST FOR THE OXIDATION OF METHANOL TO FORMALDEHYDE

[75] Inventors: Ferruccio Trifiró; Pierluigi Villa, both of Milan; Luciano Cairati, Cassano d'Adda (Milan), all of Italy

[73] Assignee: Societa' Italiana Resine S.I.R. S.p.A., Milan, Italy

[22] Filed: July 10, 1975

[21] Appl. No.: 594,891

[30] Foreign Application Priority Data
July 25, 1974  Italy................................. 25545/74

[52] U.S. Cl............................ 252/470; 260/603 HF
[51] Int. Cl.².......................................... B01J 23/88
[58] Field of Search................. 252/470; 260/603 R, 260/603 HF; 423/594

[56] References Cited
UNITED STATES PATENTS
3,716,497   2/1973   Courty............................... 252/470

Primary Examiner—W. J. Shine
Attorney, Agent, or Firm—Sughrue, Rothwell, Mion, Zinn and Macpeak

[57] ABSTRACT

A catalyst active in the oxidation of methanol to formaldehyde is prepared by forming a suspension of an amorphous precipitate by mixing an aqueous molybdate solution with an aqueous solution of a ferric salt, while maintaining an atomic ratio Mo/Fe of at least 1.5:1 in the mixture, heating the suspension at 70°–100°C for at least 30 minutes, washing the resulting precipitate with water to remove the soluble salts and at least a part of the excess of soluble molybdate not transformed into iron molybdate, thereby to ensure in the washed solid an atomic ratio Mo/Fe of from 1.5:1 to 1.7:1, and drying the washed solid at a temperature not exceeding 120°C for a period of at least 30 minutes.

The catalyst consists of iron molybdate $Fe_2(MoO_4)_3$ with an amount of free molybdenum trioxide ranging from zero to a value such that the atomic ratio Mo/Fe is from 1.5:1 to 1.7:1, and has a crystallinity degree of at least 90%.

14 Claims, No Drawings

PROCESS FOR PREPARING A CATALYST FOR THE OXIDATION OF METHANOL TO FORMALDEHYDE

The present invention relates to the production of formaldehyde by means of the catalytic oxidation of methanol, and in particular, the invention relates to an active catalyst for such an oxidation reaction and the process for the preparation of the said catalyst.

It is known that in the prior art, the preparation of formaldehyde is effected by the dehydrogenation and oxidation of methanol on metallic silver, operating in the absence of air, or by oxidation of methanol on metal oxide catalysts, in the presence of a large excess of air and at relatively low temperatures (300°–400°C).

The processes which use metal oxides as catalysts have advantages over those using metallic silver, in that they ensure higher yields of formaldehyde and the practically complete transformation of the methanol.

In consequence, there is no need to recover the unaltered methanol from the reaction products, and aqueous formaldehyde solutions which are substantially free from methanol are obtained.

Moreover, the metal oxide catalysts have a relatively long working life in conditions of use, and because of their selectivity, they permit the production of aqueous formaldehyde solutions with a very low content of formic acid.

The metal oxides suitable for this purpose are those of molybdenum and iron, with a molar ratio of $MoO_3/Fe_2O_3$ in the catalyst varying, according to the patent literature, within a wide range, such as, from 3.6:1 to about 11:1.

However, the catalysts used industrially always show a relatively high excess of molybdenum trioxide.

The reason why in the preparation of the catalysts, one uses an excess of molybdenum compound, is to be found in the need to prevent the formation of catalysts lacking in molybdenum, inasmuch as such catalysts would show a poor selectivity in the oxidation process of methanol to formaldehyde.

On the other hand, catalysts containing an excess of molybdenum trioxide are not without disadvantages.

In the reaction conditions, there is experienced, in fact, phenomena of volatilization of the molybdenum trioxide from the areas of the catalytic bed where the temperature reaches the highest values and the said molybdenum trioxide is then deposited in the colder areas at the bottom of the said bed.

This leads to a diminution of the activity and selectivity values of the catalyst in the course of time.

In the known preparations of iron and molybdenum oxide catalysts, the following steps are followed:
— the formation of a complex precipitate from solutions containing soluble salts of molybdenum and iron;
— the separation, washing and drying of the said precipitate;
— the shaping into granules of suitable form and size;
— the calcination at high temperature.

In practice these are expensive processes which comprise many successive stages, each of which must be carried out under well-defined and imperative conditions.

Thus, for example, the drying of the precipitate is effected over long periods, under controlled temperature conditions, in order to bring the content of residual water within an accurate range of values, and this for the purpose of not impairing the mechanical characteristics of the finished catalyst.

A characteristic common to the known processes in that an amorphous or substantially amorphous solid is precipitated, when the aqueous solutions of the soluble iron and molybdenum salts are mixed.

Furthermore, a fundamental operation common to all these conventional processes is the calcination treatment at high temperature which provides the catalyst with the required activity, and also imparts to it the mechanical characteristics which are essential for its use in the oxidation of methanol to formaldehyde.

The catalyst of the present invention, active in the oxidation of methanol to formaldehyde, differs from those of the prior art in that it is constituted of iron molybdate $Fe_2(MoO_4)_3$, without, or practically without, any additional free molybdenum trioxide, having a degree of crystallinity measured by X-rays, equal to at least 90%.

When it is stated that the catalyst is free or practically free of molybdenum trioxide, this means that in the catalyst, the atomic ratio of molybdenum to iron ranges from 1.5:1 up to a maximum of 1.7:1.

The process for the preparation of the catalyst according to the present invention has as its fundamental feature, the direct transformation into crystalline iron molybdate, of the amorphous or substantially amorphous precipitate obtained by contacting the aqueous solutions containing soluble salts of molybdenum and iron. The said crystalline transformation takes place in the same medium where the precipitation has been effected.

Another fundamental aspect of the process consists in the fact that the catalyst is not subjected to any calcination treatment at high temperature.

In the known processes, this calcination constitutes an indispensable stage for confering activity and mechanical resistance to the catalyst.

More particularly, the catalyst of the present invention is prepared by means of a process which comprises the following successive steps:

a. slowly mixing an aqueous solution of a soluble molybdate having a pH value of from 1.5 to 5.5 with an aqueous solution of a soluble ferric salt at a temperature of from 20° to 80°C in such proportions as to ensure in the resulting mixture an atomic ratio of molybdenum to iron of at least 1.5:1, thereby to obtain a suspension of an amorphous precipitate;

b. heating said suspension for at least 30 minutes at a temperature of from 70°C to its boiling point, thereby to transform the amorphous precipitate into iron molybdate having a degree of crystallinity of at least 90%;

c. washing the resulting precipitate with water at a temperature from ambient temperature to its boiling point to remove the soluble salts produced and at least a part of the excess of said soluble molybdate, not transformed into iron molybdate in order to ensure in the resulting washed solid an atomic ratio of molybdenum to iron ranging from 1.5:1 to 1.7:1;

d. drying said washed solid at a temperature not exceeding 120°C for a period of at least 30 minutes.

The water-soluble molybdates are usually chosen among alkali metal or ammonium molybdates. Examples of such compounds are: ammonium paramolybdate $(NH_4)_6Mo_7O_{24}\cdot4H_2O$ and ammonium dimolybdate $(NH_4)_2Mo_2O_7\cdot XH_2O$.

The water-soluble ferric salts are usually chosen from: ferric nitrate $Fe(NO_3)_3 \cdot 9H_2O$ and ferric chloride $FeCl_3 \cdot 6H_2O$.

The soluble molybdate is generally dissolved in water up to a concentration of 20 to 30 grams/liter and preferably the pH of the resulting solution is set to a value of from 1.5 to 2.8 by adding a mineral acid, for instance, nitric acid. The best results are obtained with molybdate solutions having a pH of the order of 1.8.

Separately, there is prepared an aqueous solution of the ferric salt by dissolving the said salt in water, generally up to a concentration of from 90 to 100 grams/liter. If necessary, the pH of the resulting solution is set to a value of from 0.5 to 1.5 by adding a mineral acid, for example nitric acid, the preferred values of the pH being of the order of 1.1–1.5.

The two solutions are then gradually mixed for a period of time which generally ranges from 5 to 15 minutes. When making the mixture the molybdate solution can be added to that of the iron salt, or vice-versa, or else the two solutions can be simultaneously poured into the reaction vessel. In any case, it is advisable to stir the mass, while the temperature is kept at a value of from 20° to 80°C.

The relative quantities of the two solutions are chosen in such a manner that at the end of the mixing, the atomic ratio of molybdenum to iron be equal to or greater than 1.5:1 and preferably from 1.5:1 to 1.9:1. It is not advantageous to select excessively high values for this atomic ratio, so as not to make the following washing stage too expensive. In fact, during this stage, the said atomic ratio is brought down to a value near to 1.5:1 and, anyway, not exceeding 1.7:1 by removing the excess of molybdenum compound not transformed into iron molybdate, or at least bringing it down within such limits as to obtain the above range of atomic ratios. In every case, the best results are obtained with atomic ratios of molybdenum to iron during the precipitation stage of the order of 1.6:1–1.7:1.

During the precipitation stage, there is formed a suspension of a precipitate which is amorphous, or substantially amorphous, under X-ray examination. This precipitate shows an infra-red ray spectrum with very wide bands at approximately 900 – 800 cm$^{-1}$, 600 cm$^{-1}$ and 990 cm$^{-1}$.

The suspension thus obtained is heated at a temperature of from at least 70°C up to its boiling point, for a period of time of at least 30 minutes. At this stage of the process, there may suitably be added to the suspension substances capable of promoting the transformation of the amorphous precipitate into crystalline iron molybdate.

A useful substance for this purpose is the preformed iron molybdate having an atomic ratio of molybdenum to iron ratio of 1.5:1, which under X-ray examination has a degree of crystallinity of at least 95%. This substance can be added to the reaction medium in a proportion generally not exceeding 3 wt.% and preferably of from 0.1 to 1% by weight with respect to the quantity of crystalline iron molybdate being formed.

The heating time of the suspension is generally from 30 minutes to 6 hours. Generally, heating times of the order of 3–6 hours are adhered to when operating without substances which promote the crystalline transformation. When operating in the presence of preformed crystalline iron molybdate, the heating times required to obtain the required result are typically of the order of 2–3.5 hours. In every case, the heating times should be such that the finished catalyst is of a degree of crystallinity at least equal to 90% when determined by X-ray examination.

In practice, when using solutions of ammonium paramolybdate and of ferric chloride or ferric nitrate as starting materials for the precipitation, there is noted, during the heating phase, a variation in the colour of the precipitate which turns from yellow to peagreen, and also a variation in the grain of the precipitate which assumes a crystalline consistency.

At the end of the heating, the suspension is decanted and the solid is subjected to washing after separation from the mother liquor.

The washing with water is mainly for the purpose of removing the soluble salts which are formed in the reaction between the molybdate and the ferric salt. Thus, for instance, when using for the precipitation ferric chloride and an ammonium molybdate, it is convenient to continue the washing up to the point where the washing water has a content of chloride and ammonium ions less than 0.2% by weight.

A further purpose of the washing is the total or partial removal of the molybdenum compound, not combined in the form of iron molybdate, added in excess during the precipitation stage, thereby to bring the content of free molybdenum trioxide in the finished catalyst between the limits which have been previously described.

The washing can be effected with water acidulated at a pH value in the range from 7 to 1.2, such as, for example, a pH value of 1.2–1.8, by a mineral acid such as nitric acid. It should be noted that a not acidulated washing water is preferably used at a temperature from 80°C to its boiling point, whereas an acidulated washing water is generally used at ambient temperature.

The washed solid is finally subjected to drying and at this stage it is convenient to gradually increase the temperature from ambient or near ambient values up to a maximum value not exceeding 120°C.

The latter temperature is generally maintained for a period of 30 minutes up to 15 hours, or in any event, for a period of time sufficient to cause the total or substantially total elimination of the water.

In this manner, there is obtained the catalyst of the present invention which is constituted by a solid with a crystallinity, measured under X-rays, of at least 90% and usually of the order of 95 – 98%. Moreover this solid presents an infra-red spectrum with a very narrow band at about 800 cm$^{-1}$. But instead, there is a disappearance, or at least a considerable attenuation of the bands at 600 and 990 cm$^{-1}$, typical of the precipitation product of the solutions of ferric salt and molybdate.

Moreover, the catalyst of the present invention is constituted by iron molybdate $Fe_2(MoO_4)_3$ with an amount of free molybdenum trioxide ranging from zero to a value such that the atomic ratio of molybdenum to iron is from 1.5:1 to 1.7:1.

It is noteworthy that the characteristics possessed by the catalyst at the end of the drying stage do not undergo appreciable variations, when the said catalyst is subjected to a calcination treatment at temperatures and for periods typical of the processes of the prior art, such as, for example, a calcination at 400–450°C for a period of 4 hours.

The catalyst of the present invention is conveniently used in a fixed-bed form in the preparation of formaldehyde by catalytic oxidation of methanol. The catalyst obtained after the drying stage is in powder form and therefore to make it usable in a fixed-bed it is shaped into granules of the required dimensions, by means of compression treatments of the powder, possibly followed by crushing, milling or similar operations. Finally, it is possible to mill into a fine powder the solid resulting from the drying stage, and subsequently to pelletize this powder, in the manner described in U.S. Pat. No. 3,464,931.

When preparing formaldehyde there is fed to the catalyst of the present invention a gaseous mixture containing methanol, oxygen and nitrogen, generally at a rate of from 5 to 15 N liters per ml of catalyst and per hour.

In order to avoid the hazard of explosions, it is necessary to operate outside the range of explosivity of the nitrogen-oxygen-methanol mixtures. This can be done, for example, by using air-methanol mixtures with less than 6.7% methanol by volume or nitrogen-oxygen-methanol mixtures with an oxygen content lower than 10.9% by volume.

Moreover, the formaldehyde preparation is carried out at a temperature of from 270° to 340°C and it is convenient to place the catalyst within elongated tubular reactors which are externally provided with a circulating fluid for controlling the thermal effect of the reaction.

The formaldehyde can be recovered from the reaction gases by stripping, for instance with water.

The major advantage of the catalyst of the present invention consists in its great mechanical strength, and for this reason one practically eliminates any crumbling in conditions of use. It is therefore possible to maintain a high rate of the gaseous feed steam, with consequent high output of formaldehyde.

All this takes place while maintaining high values of the methanol conversion ((typically around a molar value of 92–98%) and of the selectivity for the formaldehyde produced (typically around a molar value of 90–92% with respect to the moles of converted methanol). The mechanical strength of the catalyst allows its use for longer periods of time, in the given conditions of work, than would be the case with conventional catalysts.

The catalysts of the present invention have, relative to the industrially by known ones, a smaller content of molybdenum, thus providing an economic advantage, since molybdenum is by far the most expensive constituent element.

Finally, the process for preparing the catalyst presents remarkable simplifications relatively to the processes of the prior art.

The following experimental examples will serve to further illustrate the invention without however limiting it in any way.

EXAMPLE 1

A first aqueous solution is prepared by dissolving 6.3 grams of commercial ammonium paramolybdate $(NH_4)_6Mo_7O_{24}\cdot 4H_2O$ in 300 ml of deionized water. The pH of the solution is set to 1.8 by the addition of nitric acid.

Separately, there is prepared another aqueous solution, by dissolving 10 grams of ferric nitrate $Fe(NO_3)_3\cdot 9H_2O$ in 75 ml of deionized water. The pH of the solution of ferric salt is equal to 1.15.

Operating at ambient temperature (20°–25°C) the solution of ferric salt is poured into the stirred solution of molybdenum salt in a period of time of 5 minutes. In particular, there is used a flask equipped with a reflux cooler and a mechanical agitator.

In this manner there is obtained a suspension which is brought up to boiling point, and there are added to the boiling suspension 0.15 grams of preformed iron molybdate $Fe_2(MoO_4)_3$ having a molybdenum/iron atomic ratio of 1.5;1 and a degree of crystallinity, measured under X-rays, equal to 95%.

After 2 hours of boiling, the agitation is stopped, decantation is effected, the mother liquors are removed and the residue is filtered on a Buchner funnel. The cake of still wet residue is taken up and immersed in 400 ml of boiling water, agitating the mixture for 5 minutes. The precipitate is then removed and dried for 4 hours at 120°C.

In this manner there is obtained a solid constituted by iron molybdate $Fe_2(MoO_4)_3$, having a molybdenum/iron atomic ratio equal to 1.5, and which under X-rays, proves to have a crystallinity of 95–98%. The solid is practically free of any content of free molybdenum trioxide. The yield in iron molybdate is equal to 96–97%.

The solid which is of pale olive green colour in powder form with approximate dimensions of 100 mesh, is pelletized by means of a laboratory press, at a pressure of 100 kg/cm² in the form of tablets having dimensions of 25×10×3 mm and the tablets are crushed and sifted to granules of 12 to 20 mesh.

EXAMPLE 2

1 gram of the catalyst prepared in the way described in Example 1 is placed in a steel tubular reactor, with a diameter of 12 mm.

The reactor is fed with a gaseous stream consisting of oxygen, nitrogen and methanol in the following volumetric percentages: 23.4%, 70.0%, 6.6%. Moreover, the feed rate of the gaseous stream is of 7.1 N liters per hour and per gram of catalyst and the reaction is carried out a temperature of 320°C.

The reaction gases are stripped with water in a stripping column filled with Raschig rings.

Operating in these conditions, the methanol conversion is of 97% in moles, with a selectivity for the formaldehyde of 92% in moles with respect to the moles of converted methanol.

Furthermore, the recovered aqueous solution has a formaldehyde concentration of 20% by weight, with a content of methanol of 0.1% by weight and a content of formic acid of 0.001% by weight.

EXAMPLE 3

An aqueous solution is prepared by dissolving 40.8 grams of ammonium paramolybdate in 1800 ml of distilled water and its pH is set to 1.8 by adding concentrated nitric acid.

To this solution there is added over a period of 10 minutes an aqueous solution having a pH of 1.25 obtained by dissolving 40.3 grams of ferric chloride $FeCl_3\cdot 6H_2O$ in 450 ml of deionized water.

Following the procedure described in Example 1, the suspension obtained in this manner is brought to boiling point and there are added 0.6 grams of the preformed iron molybdate used in the first Example.

After 2.5 hours of boiling, the solid is decanted, the mother liquors are removed and the residue filtered.

The residue on the filter is washed, at ambient temperature, with 300 ml of water acidulated up to a pH of 1.7 with nitric acid, and then with water.

The solid is dried at 120°C for 15 hours and one obtains 42.2 grams of a product which under gravimetric determination, shows an atomic ratio of molybdenum to iron equal to 1.67:1.

The said solid whose crystallinity, measured by X-ray analysis, is of 90%, is constituted by 92.3% of crystalline iron molybdate, the remainder being free molybdenum trioxide.

The solid is shaped into granules as described in the first Example.

EXAMPLE 4

The formaldehyde is prepared by oxidation of the methanol, following the procedure of Example 2, but using the catalyst described in Example 3. In this manner, the methanol conversion is of 92% in moles, and the selectivity for the formaldehyde is of 90% in moles, with respect to the moles of converted methanol.

The recovered aqueous solution contains formaldehyde (30% by weight), methanol (0.2% by weight) and formic acid (0.05% by weight).

EXAMPLE 5 (COMPARATIVE)

The procedure is the same as in Example 1. The resulting iron molybdate powder is calcined at 400°C for 4 hours. At the end of this treatment, it was noted no appreciable variation in the characteristics of the said powder.

EXAMPLE 6

An aqueous solution is prepared by dissolving 100 grams of ammonium paramolybdate in 4500 ml of water, and acidified to a pH of 1.82 with concentrated nitric acid.

Separately, an aqueous solution is prepared by dissolving 100 grams of ferric chloride in 1100 ml of deionized water. This last solution has a pH of 1.32.

Operating at ambient temperature, the molybdate solution is poured into that of iron salt in a period of 15 minutes, keeping the mass agitated.

The mixture is heated at boiling point for 3 hours after adding 1.0 gram of the preformed iron molybdate used in Example 1. The solid separated by decantation, removal of the mother liquors and filtration, is washed with 1 liter of water acidulated with nitric acid at a pH of 1.72, and then with water.

After drying for 5 hours at 120°C a solid is obtained in powder form of the following characteristics: pale pea-green colour, atomic ratio of molybdenum to iron of 1.5:1 and 95% crystallinity under X-ray examination.

All the powder is pelletized in the form of small cylinders of 5×5 mm with an internal bore of 1.5 mm, using a semi-industrial pelletizing machine.

EXAMPLE 7

The catalyst prepared as described in Example 6 is introduced in an AISI 316 steel monotubular reactor, 60 cm in height and 5 cm in internal diameter.

The reactor is fed with a gaseous mixture preheated at 230°C, composed of methanol (6.5% in volume), oxygen (10% by volume), the remaining percentage being nitrogen. The gaseous mixture is fed in at the rate of 10 N liters per hour and per ml of catalyst.

Moreover, the reaction is carried out at 280°C and the gaseous mixture issuing from the reactor is stripped with water.

In this manner, one obtains a methanol conversion of 97% in moles, with a selectivity for the formaldehyde of 90% in moles, with respect to the moles of converted methanol.

The recovered aqueous solution contains formaldehyde (36.2% by weight), methanol (0.5% by weight) and formic acid (0.008% by weight). After 3 months of operation at the above temperature, the pressure loss was insignificant, and this indicated that the catalyst forms practically no powder.

In this connection, it should be noted that the reaction temperature (280°C) is sensibly lower than that used in the commercially known processes (300°–400°C). The catalyst of the invention is therefore more active. It should also be noted that the catalyst maintained its activity at a constant level for 3 months without needing any increase of the reaction temperature. This is a further advantage of the catalyst of the invention, since it is known that the reaction temperature must be increased in proportion as the catalyst activity decreases.

EXAMPLE 8

The procedure is the same as in Example 1, with the only difference that the solution of ferric salt is added to the molybdate solution, operating at 75°C.

Operating as described in Example 1, one obtains an iron molybdate catalyst $Fe_2(MoO_4)_3$ with an atomic ratio of molybdenum to iron of 1.51:1 and a crystallinity under X-rays of 98%.

We claim:

1. A method for the preparation of a catalyst active in the oxidation of methanol to formaldehyde, which comprises:
   a. slowly mixing an aqueous solution of a soluble molybdate having a pH value of from 1.5 to 5.5 with an aqueous solution of a soluble ferric salt at a temperature of from 20° to 80°C in such proportions as to ensure in the resulting mixture an atomic ratio of molybdenum to iron of at least 1.5:1, thereby to obtain a suspension of an amorphous precipitate;
   b. heating said suspension for at least 30 minutes at a temmperature of from 70°C to its boiling point, thereby to transform the amorphous precipitate into iron molybdate having a degree of crystallinity of at least 90%;
   c. washing the resulting precipitate with water at a temperature from ambient temperature to its boiling point to remove the soluble salts produced and at least a part of the excess of said soluble molybdate, not transformed into iron molybdate, in order to ensure in the resulting washed solid an atomic ratio of molybdenum to iron ranging from 1.5:1 to 1.7:1;
   d. drying said washed solid at a temperature not exceeding 120°C for a period of at least 30 minutes.

2. The method of claim 1, which comprises mixing an aqueous solution containing from 20 to 30 grams/liter of soluble molybdate with an aqueous solution containing from 90 to 140 grams/liter of soluble ferric salt.

3. The method of claim 1, wherein the aqueous solution of molybdate has a pH value of from 1.5 to 2.8.

4. The method of claim 3, wherein said pH value is of the order of 1.8.

5. The method of claim 1, wherein the aqueous solution of ferric salt has a pH value of from 0.5 to 1.5.

6. The method of claim 1, wherein the aqueous solution of ferric salt has a pH value of from 1.1 to 1.5.

7. The method of claim 1, which comprises mixing said aqueous solutions for a period of from 5 to 15 minutes.

8. The method of claim 1, which comprises mixing said aqueous solutions in such proportions as to ensure in the resulting mixture an atomic ratio of molybdenum to iron of from 1.5:1 to 1.9:1.

9. The method of claim 8, wherein said atomic ratio of molybdenum to iron in the resulting mixture is from 1.6:1 to 1.7:1.

10. The method of claim 1, wherein said suspension is heated for a period of from 30 minutes to 6 hours.

11. The method of claim 1, wherein said suspension is heated in the presence of preformed iron molybdate having an atomic ratio of molybdenum to iron of 1.5:1 and a degree of crystallinity under X-ray examination of at least 95%.

12. The method of claim 1, wherein said resulting precipitate is washed with water acidulated at a pH value in the range from 7 to 1.2.

13. The method of claim 12, wherein said acidulated water is at a pH value of from 1.8 to 1.2.

14. The method of claim 1, wherein said washed solid is dried for a period of from 30 minutes to 15 hours.

* * * * *